United States Patent [19]

Specht et al.

[11] Patent Number: 5,635,343

[45] Date of Patent: Jun. 3, 1997

[54] ULTRAVIOLET ABSORBING COMPOUNDS AND PHOTOGRAPHIC ELEMENTS CONTAINING THEM

[75] Inventors: Donald P. Specht; Donald R. Diehl, both of Rochester, N.Y.

[73] Assignee: Eastman Kodak Company, Rochester, N.Y.

[21] Appl. No.: 520,153

[22] Filed: Aug. 28, 1995

Related U.S. Application Data

[63] Continuation-in-part of Ser. No. 315,060, Sep. 29, 1994, abandoned.

[51] Int. Cl.$^6$ ................................................. G03C 1/815
[52] U.S. Cl. ........................ 430/512; 430/591; 430/931
[58] Field of Search ........................................ 430/512, 591, 430/522, 931; 252/589

[56] References Cited

U.S. PATENT DOCUMENTS

| | | | |
|---|---|---|---|
| Re. 29,168 | 4/1977 | Heleltine et al. | 96/84 |
| 2,185,182 | 1/1940 | Brooker | 430/591 |
| 3,282,669 | 11/1966 | Jones et al. | 430/522 |
| 3,537,858 | 11/1970 | Wise | 96/107 |
| 3,579,344 | 5/1971 | Webster | 430/591 |
| 3,674,782 | 7/1972 | Eldredge et al. | 260/240.4 |
| 3,772,278 | 11/1973 | Jeffreys et al. | 260/240 |
| 4,028,112 | 6/1977 | Sato et al. | 96/84 |
| 4,044,773 | 8/1977 | Lewis et al. | 96/115 |
| 4,105,545 | 8/1978 | Tani | 96/122 |
| 4,110,115 | 8/1978 | Sugiyama et al. | 96/84 |
| 4,294,916 | 10/1981 | Postle et al. | 430/522 |
| 4,360,588 | 11/1982 | Postle | 430/512 |
| 4,563,406 | 1/1986 | Ohbayashi et al. | 430/513 |
| 4,690,883 | 9/1987 | Kubodera et al. | 430/591 |
| 4,940,654 | 7/1990 | Diehl et al. | 430/522 |
| 5,085,970 | 2/1992 | Kameoka et al. | 430/264 |

FOREIGN PATENT DOCUMENTS

| | | |
|---|---|---|
| 1 541 936 | 4/1976 | European Pat. Off. |
| J6-3034-537-A | 2/1988 | Japan. |
| J6-3035-538-A | 2/1988 | Japan. |
| JO-1013-543-A | 1/1989 | Japan. |
| 2083241 | 4/1984 | United Kingdom. |

OTHER PUBLICATIONS

Collection of Czehoslovak Chemical Communications, vol. 44, No. 5, 1979, Prague CS, pp. 1413-1422, Vautoua et al. Organic Magnetic Resonance, vol. 11, No. 11, Nov. 1978, pp. 555-560.

*Primary Examiner*—Richard L. Schilling
*Attorney, Agent, or Firm*—Edith A. Rice

[57] ABSTRACT

A substantially inert ultraviolet absorbing compound, and photographic elements containing them, which compound has a peak absorption at less than 400 nm and being of formula (I):

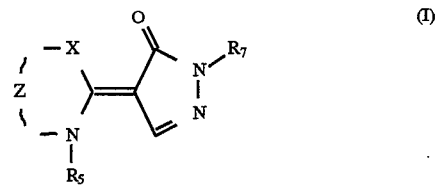

wherein:
X is O or $NR_8$, Z represents the atoms necessary to complete a 5-membered or 6-membered heterocyclic ring which includes X and N, and the 3-position of the pyrazolone ring may independently be substituted or unsubstituted;

$R_5$ is alkyl, alkenyl, or arylalkyl any of which may be substituted or unsubstituted, or $R_5$ may form a ring with a 3-position substituent on the pyrazolone ring or a 4-position substituent on the benzo ring;

$R_7$ is alkyl, alkenyl, aryl, or heterocycle, any of which may be substituted or unsubstituted, or H; and $R_8$ is alkyl, alkenyl, or arylalkyl any of which may be substituted or unsubstituted, or H.

18 Claims, No Drawings

ULTRAVIOLET ABSORBING COMPOUNDS AND PHOTOGRAPHIC ELEMENTS CONTAINING THEM

This application is a continuation in part of U.S. patent application Ser. No. 08/315,060 filed Sep. 29, 1994, now abandoned, the entire disclosures of which are incorporated herein by reference.

FIELD OF THE INVENTION

This invention relates to particular ultraviolet absorbing compounds, photographic elements containing them, and a method of forming such elements and developing them.

BACKGROUND OF THE INVENTION

Many organic compounds such as dyes, polymers and natural products can be damaged or destroyed either by the direct absorption of ultraviolet light, or by the action of free radicals produced by the absorption of ultraviolet light. One method of protecting such materials is by overcoating or imbibing the material to be protected with an ultraviolet light ("UV") absorber. A UV absorber is a material which is capable of absorbing radiation in the range of about 250–400 nm and dissipating the absorbed energy while undergoing little or no destruction itself. Although there is a great need for such materials, there are only a very few classes that have been found to possess the required stability. These are the O-hydroxyphenyl benzotriazoles, the O-hydroxybenzophenones, the phenysalicylates, and certain butadiene and arylidene materials containing both donor and acceptor substituents.

Photographic elements in particular have specific requirements for a UV absorber. Typical photographic elements use silver halide emulsions, the silver halide having a native sensitivity to ultraviolet UV radiation ("UV"). Such UV sensitivity is usually undesirable in that it produces an image on the photographic element which is not visible to the human eye. In addition, in the case of color photographic elements, in particular, color dye images formed on the light sensitive emulsion layers by color development easily undergo fading or discoloration due to the action of UV. Also, color formers, or so-called couplers, remaining in the emulsion layers are subject to the action of UV to form undesirable color stains on the finished photographs. The fading and the discoloration of the color images are easily caused by UV of wavelengths near the visible region, namely, those of wavelengths from 300 to 400 nm. For the foregoing reasons, photographic elements typically incorporate a UV absorbing material in an upper layer. The O-hydroxyphenylbenzotriazole class of UV absorbers has been particularly useful for photographic purposes since the spectrum of each covers a broad region of the UV but is still sharp cutting on the long wavelength side near 400 nm.

Given the very few classes of compounds which are suitable as UV absorbers, it is desirable to have new classes of UV absorbers particularly for application in photographic elements, which UV absorbers possess good photostability and high molecular extinction coefficients, so that less material is used to give the same amount of absorption.

SUMMARY OF THE INVENTION

The present invention provides ultraviolet absorbing compounds, and photographic elements containing them, which ultraviolet absorbing compound has a peak absorption at less than 400 nm and has the formula (I) below:

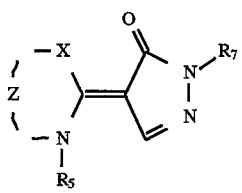

wherein:

X is O or $NR_8$, Z represents the atoms necessary to complete a 5-membered or 6-membered heterocyclic ring which includes X and N, and the 3-position of the pyrazolone ring may independently be substituted or unsubstituted;

$R_5$ is alkyl, alkenyl, or arylalkyl any of which may be substituted or unsubstituted, or $R_5$ may form a ring with a 3-position substituent on the pyrazolone ring or a 4-position substituent on the benzo ring;

$R_7$ is alkyl, alkenyl, aryl, or heterocycle, any of which may be substituted or unsubstituted, or H; and $R_8$ is alkyl, alkenyl, or arylalkyl any of which may be substituted or unsubstituted, or H.

EMBODIMENTS OF THE INVENTION

First, by reference to "under", "above", "below", "upper", "lower" or the like terms in this application in relation to layer structure of a photographic element, is meant the relative position in relation to light to when the element is exposed in a normal manner. "Above" or "upper" would mean closer to the light source when the element is exposed normally, while "below" or "lower" would mean further from the light source. Since a typical photographic element has the various layers coated on a support, "above" or "upper" would mean further from the support, while "below" or "under" would mean closer to the support. Also, by reference to "substantially inert" in relation to a UV absorbing compound in a photographic element of the present application, is meant that less than 50% of the compound, by weight, is destroyed or otherwise removed from the photographic element as a result of processing (i.e., developing, bleaching and fixing), particularly by processing in accordance with the well known C41 color negative development process, which is described in *British Journal of Photography Annual* 1979 pg 204. By reference to simply "inert" in the foregoing context, is meant that less than 10% of the compound, by weight, is destroyed or otherwise removed from the element as a result of processing, particularly by processing in accordance with the C41 process. For the UV absorbing compound alone (not present in any element), these figures would be measured with the UV absorbing compound in an overcoat layer (that is, above all light sensitive layers) of a typical photographic negative element. Additionally, reference to the "peak absorption" of the ultraviolet absorbing compound means the maximum absorption in the region of 300-700 nm.

Formula (I) above includes structures of the following formula:

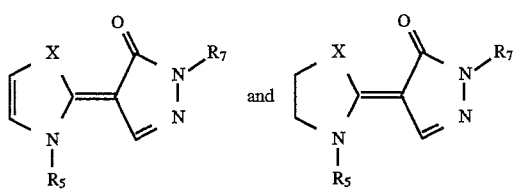

in which the 5-membered ring containing X and N may be unsubstituted or substituted (the substituents including any of those particular substituents for $R_1$ to $R_4$ described below).

The ultraviolet absorbing compound may particularly be of formula (Ia) or (Ib) below:

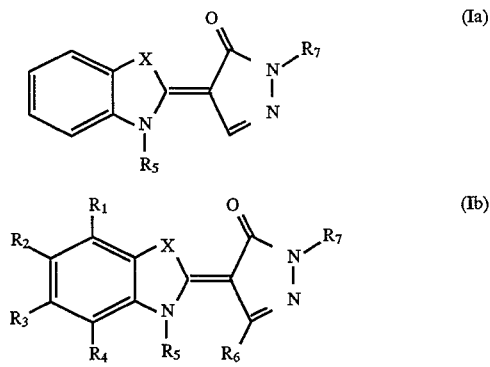

In the above forumula (Ia) or (Ib) X, $R_5$ and $R_7$ are as defined above, and the benzo ring and the 3-position of the pyrazolone ring may independently be substituted or unsubstituted. $R_1$, $R_2$, $R_3$, $R_4$ and $R_6$ may be the same or different and any of them may be alkyl, alkenyl, aryl, heterocycle, alkoxycarbonyl, aryloxycarbonyl, alkoxy, aryloxy, sulfonamide, amino, imino, or amido, any of which may be substituted or unsubstituted, or hydrogen, hydroxy, cyano, or halogen, or combinations of $R_1$ to $R_4$ can be taken to form an alicyclic, carbocyclic or heterocyclic ring (groups such as sulfonic acid groups would be undesirable as they may result in a substantial amount of the UV absorbing compound washing out during processing, that is resulting in a compound which is not substantially inert). $R_5$ is alkyl, alkenyl, or arylalkyl any of which may be substituted or unsubstituted, or $R_5$ may form a ring with $R_4$ or $R_6$. Where any of the foregoing carbon containing groups may particularly have from 1 to 20, 1 to 8, or 1 to 6 carbon atoms in total.

Additionally, the ultraviolet absorber may more particularly be of formula (Ic):

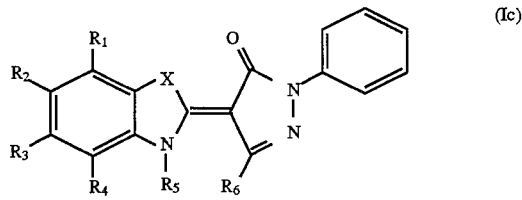

wherein the N-phenyl ring may be substituted or unsubstituted.

The halogen atoms described above may particularly include chlorine or bromine. Any of the substituted or unsubstituted alkyl or alkenyl described above (either as separate groups or part of another group as in alkoxycarbonyl) may particularly include those with 1 to 20 carbon atoms, or more particularly may be a "lower" alkyl or alkenyl (that is, having from 1 to 6 carbon atoms.

Examples of substituted or unsubstituted alkyl include a methyl group, an ethyl group, an n-propyl group, an isopropyl group, a butyl group, a tert-butyl group, an n-amyl group, an n-octyl group, a tert-octyl group, a methoxyethyl group, an ethoxyethyl group, a hydroxyethyl group, a benzyl or a cyanoethyl group. Any of the aryl mentioned may particularly have from 6 to 20 atom carbon atoms (for example, a phenyl group, a tolyl group, a mesityl group, or the like). Any alkoxy group may particularly have from 1 to 20 carbon atoms (for example, a methoxy group, an ethoxy group, a propoxy group, a butoxy group, an ethoxyethoxy group, or the like). Any aryloxy group may also particularly have from 6 to 20 carbon atoms (for example, a phenoxy group, or a 4-methylphenoxy group, or the like). Any amino described includes an aminoalkyl or arylamino having from 1 to 20 carbon atoms, or 1 to 6 carbon atoms. Examples include a methylamino group, an ethylamino group, anilino group. Amido or imino may also have from 1 to 20 carbon atoms (or 1 to 6 carbon atoms). Amido particularly includes groups such as acetylamino. Examples of heterocyclic rings include thienyl, furyl and pyrrolyl.

The substituents on the above described groups when described as "substituted", as well as on the benzo ring and N-phenyl ring, can include any known substituents, such as halogen (for example, chloro, fluoro, bromo, iodo), alkoxy (particularly of 1 to 8 or 1 to 6 carbon atoms, for example, methoxy, ethoxy), substituted or unsubstituted alkyl (particularly of 1 to 8 or 1 to 6 carbon atoms, for example, methyl, trifluoromethyl), alkenyl, thioalkyl (for example, methylthio or ethylthio), substituted and unsubstituted aryl (particularly of 6 to 18 carbon atoms, for example, phenyl) heterocyclic structures (for example, thienyl, furyl, pyrrolyl), alkoxy and others known in the art. Such alkyl and alkoxy substituents may specifically include "lower" alkyl and alkoxy, that is having from 1 to 6 carbon atoms, for example, methyl, ethyl, and the like. Additionally, substituents may form bridged linkages. Further, with regard to any alkyl group, alkylene group or alkenyl group, it will be understood that these can be branched or unbranched and include ring structures. Additonally, it will be understood that $R_1$ through $R_4$ can form a benzo, naphtho or other aromatic ring structure fused with the benzo ring shown in formula (I). Such fused rings can also be unsubstituted or substituted with any of the described substituents for the benzo ring shown in formula (Ia). However, UV absorbing compounds of formula (I) (which of course includes formula (Ia) and (Ib)) in which optionally $R_1$ through $R_4$ could exclude such fused rings, are also contemplated.

A photographic element of the present invention will additionally have at least one light-sensitive layer containing a light sensitive silver halide emulsion. Additionally, photographic elements of the present invention typically also have a non-light sensitive layer which does not contain any light-sensitive silver halide emulsion, the ultraviolet absorber described in formula (Ia), (Ib) or (Ic) being located in the non-light sensitive layer. For color elements, as described below, they will typically have at least three layers containing light sensitive silver halide emulsions. In any event, regardless of the number of light sensitive silver halide emulsion containing layers, the non-light sensitive layer in which the ultraviolet absorber of formula (I) is located, may particularly be above all of the light-sensitive layers of the element or below all the light sensitive layers, or on the backside of a transparent support (that is, on the side of the support opposite from the side bearing the light sensitive layer or layers). Preferably, all of the light sensitive layers of the element do not contain any surface fogged silver halide emulsion.

As to the amount of the ultraviolet absorbing compound of formula (Ia), (Ib) or (Ic) in photographic elements of the present invention, preferably such amount is between 0.10 g/m² to 2.0 g/m² (more preferably between 0.5 g/m² to 1 g/m²). Photographic elements of the present invention may also be constructed such that the amount of ultraviolet absorber of formula (I) in any layer containing light sensitive silver halide is less than $10^{-8}$ moles per mole of silver halide. It will be understood that a layer "containing light sensitive silver halide" in this context is one which will contain silver halide in more than just trace amounts and in sufficient quantity to form a visible image (for example, more than 1 mg/m² or more typically more than 10 mg/m²).

Photographic elements of the present invention may include those which are unexposed and unprocessed as well as those which have been processed (usually following exposure). By "processed" is meant treating the element with at least a developer and a fixer, no matter what the nature of the final image is (for example, a silver image as is the case typically in black and white elements, or a dye image as is typically the case in color elements, either of which may be a positive or negative image).

The present invention also includes a method of developing photographic elements of the present invention to obtain a final negative image. By a negative image is meant one which is a negative of the scene or image to which the element was exposed (thus, typical photographic negatives or color paper have a final negative image when processed).

A method of forming a photographic element of the present invention is further provided. The method includes coating the light-sensitive layer on an element portion comprising at least a base, and also coating the non-light sensitive layer containing the ultraviolet absorber (either beneath the light sensitive layer or above it).

Examples of ultraviolet absorbing compounds used in elements of the present invention include Dye 1 to Dye 4 below:

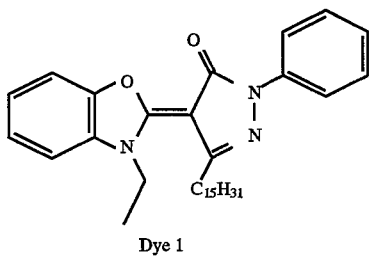

Dye 1

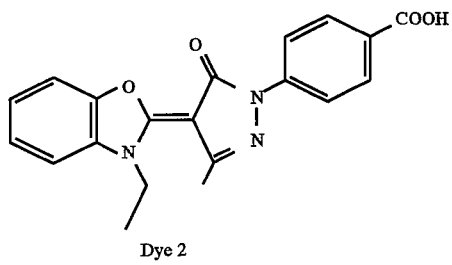

Dye 2

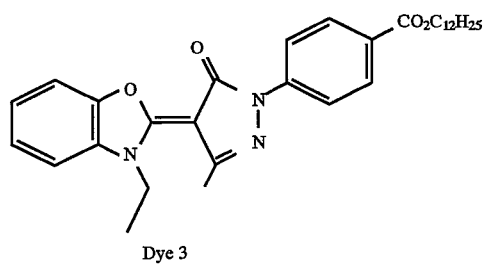

Dye 3

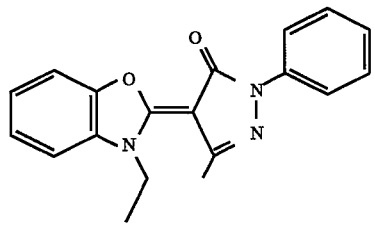

Dye 4

-continued

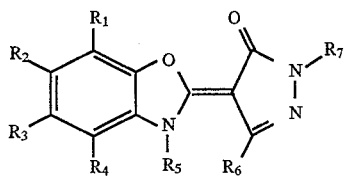

| Dye | R1 | R2 | R3 | R4 | R5 | R6 | R7 |
|---|---|---|---|---|---|---|---|
| 5 | Cl | H | H | Cl | Me | Me | Ph |
| 6 | MeO | H | Me | H | Me | Me | Me |
| 7 | H | Me | Me | H | Me | Et | t-Bu |
| 8 | H | H | H | Ph | Et | Et | Me |
| 9 | H | NH2SO2Et | Cl | H | Et | Pr | PhCO2C12H25 |
| 10 | H | NH2 | Cl | H | Et | Pr | Ph |
| 11 | H | NHCOPr | Cl | H | Pr | Bu | Me |
| 12 | H | H | t-Bu | H | Pr | Bu | t-Bu |
| 13 | H | H | C10H21 | H | Pr | OMe | Me |
| 14 | H | Me | C6H13 | H | Bu | Bu | PhCO2C12H25 |
| 15 | H | Me | Ph | H | Bu | C8H17 | Ph |
| 16 | H | NHCOPr | Ph | H | C8H17 | Me | Me |
| 17 | MeO | Et | CO2Me | H | C10H21 | Me | t-Bu |
| 18 | H | Et | Me | H | CH2OBu | CO2Et | Me |
| 19 | H | Et | Et | H | CH2CH2Ac | CONHMe | PhCO2C12H25 |
| 20 | H | Et | Cl | H | Pr | CONH2 | Me |
| 21 | H | Et | Ph | H | CH2Ph | COCH3 | Me |
| 22 | H | Et | NH2 | H | CH2CO2Et | CO2Pr | Et |
| 23 | H | Et | PrSO2NH | H | EtCN | H | Et |

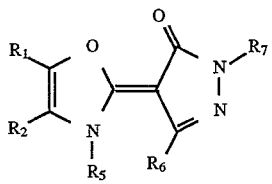

| Dye | R1 | R2 | R5 | R6 | R7 |
|---|---|---|---|---|---|
| 24 | H | H | Me | H | Me |
| 25 | Me | Me | Et | H | Et |
| 26 | Ph | Ph | Me | Me | H |
| 27 | CH2OH | H | Et | Me | Ph |
| 28 | Pr | H | C8H17 | Me | Ph |
| 29 | H | Et | CH2CH2CO2Et | Me | Ph |
| 30 | H | MeOPh | Me | Et | PhCO2C12H25 |
| 31 | H | C5H11 | Et | CO2Et | t-Bu |
| 32 | Me | Me | Me | Me | Ph |
| 33 | H | Ph | Et | Me | Ph |

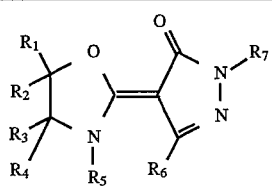

| Dye | R1 | R2 | R3 | R4 | R5 | R6 | R7 |
|---|---|---|---|---|---|---|---|
| 34 | Me | H | H | Me | Me | H | Me |
| 35 | Me | H | H | H | C8H17 | H | Et |
| 36 | Me | H | H | H | Et | Me | H |
| 37 | H | H | Me | H | Me | Me | Ph |
| 38 | H | H | Me | H | Et | Me | Ph |
| 39 | H | H | Me | Me | Me | Me | Ph |
| 40 | H | H | Me | Me | Et | Et | PhCO2Bu |
| 41 | H | H | Me | Me | Pr | CO2Et | t-Bu |
| 42 | H | H | Et | H | Me | Me | Ph |
| 43 | H | H | CH2OH | H | Me | Me | Ph |

-continued

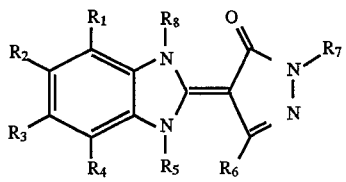

| Dye | R1 | R2 | R3 | R4 | R5 | R6 | R7 | R8 |
|---|---|---|---|---|---|---|---|---|
| 44 | H | H | H | H | Me | Me | Ph | H |
| 45 | H | Cl | H | H | Me | Me | Me | H |
| 46 | H | Cl | Cl | H | Me | Et | t-Bu | H |
| 47 | H | H | Cl | H | Me | Et | Me | H |
| 48 | H | H | H | H | Et | Pr | PhCO2C8H17 | H |
| 49 | H | Cl | H | H | Et | Pr | Ph | H |
| 50 | H | Cl | Cl | H | Et | Bu | Me | H |
| 51 | H | H | Cl | H | Et | Bu | t-Bu | H |
| 52 | H | H | H | H | Me | OMe | Me | Me |
| 53 | H | Cl | H | H | Me | Bu | PhCO2C8H17 | Me |
| 54 | H | Cl | Cl | H | Me | C8H17 | Ph | Me |
| 55 | H | H | Cl | H | Me | Me | Me | Me |
| 56 | H | H | H | H | Et | Me | H | Et |
| 57 | H | Cl | H | H | Et | CO2Et | Me | Et |
| 58 | H | Cl | Cl | H | Et | CONHMe | PhCO2C8H17 | Et |
| 59 | H | H | Cl | H | Et | CONH2 | Me | Et |

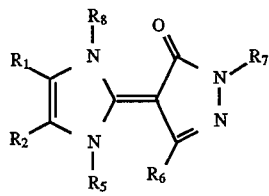

| Dye | R1 | R2 | R5 | R6 | R7 | R8 |
|---|---|---|---|---|---|---|
| 60 | H | H | Me | Et | t-Bu | H |
| 61 | Me | Me | Et | Et | Me | Me |
| 62 | Et | Et | Bu | Pr | PhCO2C12H25 | Et |
| 63 | Ph | Ph | C12H25 | Pr | Ph | —CH=CH2 |
| 64 | H | H | —CH=CH2 | Bu | Me | Ph |
| 65 | Me | Me | Bu | Bu | t-Bu | H |
| 66 | Et | Et | Et | CO2Bu | Me | Me |
| 67 | Ph | Ph | Me | Bu | PhCO2C12H25 | Et |
| 68 | Me | Me | CH2Ph | C8H17 | Ph | H |
| 69 | Et | Et | Ch2Ph | Me | Me | C7H15 |

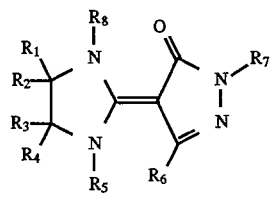

| Dye | R1 | R2 | R3 | R4 | R5 | R6 | R7 | R8 |
|---|---|---|---|---|---|---|---|---|
| 70 | H | H | H | H | Et | Bu | t-Bu | Me |
| 71 | H | Me | Me | H | Bu | Bu | Me | Et |
| 72 | H | Et | Et | H | CH2CH2OH | CO2Bu | PhCO2C8H17 | CH2Ph |
| 73 | Me | Me | Me | Me | Ph | Bu | Ph | i-Pr |
| 74 | Me | Me | Me | Me | CH2Ph | C8H17 | Me | CH2CN |
| 75 | H | H | Et | Et | Et | Me | t-Bu | H |

The photographic elements made by the method of the present invention can be single color elements or multicolor elements. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In a alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like. All of these can be coated on a support which can be transparent or reflective (for example, a paper support). Photographic elements of the present invention may also usefully include a magnetic recording material as described in *Research Disclosure*, Item 34390, November 1992, or a transparent magnetic recording layer such as a layer containing magnetic particles on the underside of a transparent support as in U.S. Pat. Nos. 4,279,945 and 4,302,523. The element typically will have a total thickness (excluding the support) of from 5 to 30 microns. While the order of the color sensitive layers can be varied, they will normally be red-sensitive, green-sensitive and blue-sensitive, in that order on a transparent support, with the reverse order on a reflective support being typical.

In the following discussion of suitable materials for use in elements of this invention, reference will be made to *Research Disclosure*, December 1989, Item 308119, published by Kenneth Mason Publications, Ltd., Dudley Annex, 12a North Street, Emsworth, Hampshire P010 7DQ, ENGLAND, which will be identified hereafter by the term "Research Disclosure I." The Sections hereafter referred to are Sections of the Research Disclosure I.

The silver halide emulsions employed in the elements of this invention can be either negative-working, such as surface-sensitive emulsions or unfogged internal latent image forming emulsions, or direct positive emulsions of the unfogged, internal latent image forming type which are positive working when development is conducted with uniform light exposure or in the presence of a nucleating agent. Suitable emulsions and their preparation as well as methods of chemical and spectral sensitization are described in Sections I through IV. Color materials and development modifiers are described in Sections V and XXI. Vehicles which can be used in the elements of the present invention are described in Section IX, and various additives such as brighteners, antifoggants, stabilizers, light absorbing and scattering materials, hardeners, coating aids, plasticizers, lubricants and matting agents are described, for example, in Sections V, VI, VIII, X, XI, XII, and XVI. Manufacturing methods are described in Sections XIV and XV, other layers and supports in Sections XIII and XVII, processing methods and agents in Sections XIX and XX, and exposure alternatives in Section XVIII.

With negative working silver halide a negative image can be formed. Optionally a positive (or reversal) image can be formed although a negative image is typically first formed.

The photographic elements of the present may also use colored couplers (e.g. to adjust levels of interlayer correction) and masking couplers such as those described in EP 213,490; Japanese Published Application 58-172,647; U.S. Pat. No. 2,983,608; German Application DE 2,706, 117C; U.K. Patent 1,530,272; Japanese Application A-113935; U.S. Pat. No. 4,070,191 and German Application DE 2,643,965. The masking couplers may be shifted or blocked.

The photographic elements may also contain materials that accelerate or otherwise modify the processing steps of bleaching or fixing to improve the quality of the image. Bleach accelerators described in EP 193,389; EP 301,477; U.S. Pat. Nos. 4,163,669; 4,865,956; and 4,923,784 are particularly useful. Also contemplated is the use of nucleating agents, development accelerators or their precursors (UK Patent 2,097,140; U.K. Patent 2,131,188); electron transfer agents (U.S. Pat. Nos. 4,859,578; 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The elements may also contain filter dye layers comprising colloidal silver sol or yellow and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. Nos. 4,420,556; and 4,543, 323.) Also, the couplers may be blocked or coated in protected form as described, for example, in Japanese Application 61/258,249 or U.S. Pat. No. 5,019,492.

The photographic elements may further contain other image-modifying compounds such as "Developer Inhibitor-Releasing" compounds (DIR's). Useful additional DIR's for elements of the present invention, are known in the art and examples are described in U.S. Pat. Nos. 3,137,578; 3,148, 022; 3,148,062; 3,227,554; 3,384,657; 3,379,529; 3,615, 506; 3,617,291; 3,620,746; 3,701,783; 3,733,201; 4,049, 455; 4,095,984; 4 126,459; 4,149,886; 4,150,228; 4,211, 562; 4,248,962; 4 259,437; 4,362,878; 4,409,323; 4,477, 563; 4,782,012; 4 962,018; 4,500,634; 4,579,816; 4,607, 004; 4,618,571; 4 678,739; 4,746,600; 4,746,601; 4,791, 049; 4,857,447; 4 865,959; 4,880,342; 4,886,736; 4,937, 179; 4,946,767; 4 948,716; 4,952,485; 4,956,269; 4,959, 299; 4,966,835; 4 985,336 as well as in patent publications GB 1,560,240; GB 2,007,662; GB 2,032,914; GB 2,099, 167; DE 2,842,063, DE 2,937,127; DE 3,636,824; DE 3,644,416 as well as the following European Patent Publications: 272,573; 335,319; 336,411; 346, 899; 362, 870; 365,252; 365,346; 373,382; 376,212; 377,463; 378,236; 384,670; 396,486; 401,612; 401,613.

DIR compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference.

It is also contemplated that the concepts of the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England, incorporated herein by reference. The emulsions and materials to form elements of the present invention, may be coated on pH adjusted support as described in U.S. Pat. No. 4,917,994; with epoxy solvents (EP 0 164 961); with additional stabilizers (as described, for example, in U.S. Pat. Nos. 4,346,165; 4,540,653 and 4,906, 559); with ballasted chelating agents such as those in U.S. 4,994,359 to reduce sensitivity to polyvalent cations such as calcium; and with stain reducing compounds such as described in U.S. Pat. Nos. 5,068,171 and 5,096,805. Other compounds useful in the elements of the invention are disclosed in Japanese Published Applications 83-09,959; 83 62,586; 90 072,629, 90 072,630; 90 072,632; 90-072,633; 90 072,634; 90 077,822; 90 078,229; 90-078,230; 90-079, 336; 90-079,338; 90-079,690; 90-079,691; 90-080,487; 90-080,489; 90-080,490; 90-080,491; 90-080,492; 90-080, 494; 90-085,928; 90-086,669; 90-086,670; 90-087,361; 90-087,362; 90-087,363; 90-087,364; 90-088,096; 90-088, 097; 90-093,662; 90-093,663; 90-093,664; 90-093,665; 90-093,666; 90-093,668; 90-094,055; 90-094,056; 90-101, 937; 90-103,409; 90-151,577.

The silver halide used in the photographic elements of the present invention may be silver iodobromide, silver bromide, silver chloride, silver chlorobromide, silver chloroiodobromide, and the like. The type of silver halide grains preferably include polymorphic, cubic, and octahedral. The grain size of the silver halide may have any distribution known to be useful in photographic compositions, and may be either polydipersed or monodispersed. Particularly useful in this invention are tabular grain silver halide emulsions. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $$T = ECD/t^2$$

where

ECD is the average equivalent circular diameter of the tabular grains in microns and t is the average thickness in microns of the tabular grains.

The average useful ECD of photographic emulsions can range up to about 10 microns, although in practice emulsion ECD's seldom exceed about 4 microns. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micron) tabular grains. To achieve the lowest levels of granularity it is preferred to that aim tabular grain projected areas be satisfied with ultrathin (t<0.06 micron) tabular grains. Tabular grain thicknesses typically range down to about 0.02 micron. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0.017 micron.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions tabular grains satisfying the stated thickness criteria above account for at least 70 percent of the total grain projected area. In the highest performance tabular grain emulsions tabular grains satisfying the thickness criteria above account for at least 90 percent of total grain projected area.

Suitable tabular grain emulsions can be selected from among a variety of conventional teachings, such as those of the following: Research Disclosure, Item 22534, January 1983, published by Kenneth Mason Publications, Ltd., Emsworth, Hampshire P010 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069 and 5,061,616.

The silver halide grains to be used in the invention may be prepared according to methods known in the art, such as those described in Research Disclosure I and James, The Theory of the Photographic Process. These include methods such as ammoniacal emulsion making, neutral or acid emulsion making, and others known in the art. These methods generally involve mixing a water soluble silver salt with a water soluble halide salt in the presence of a protective colloid, and controlling the temperature, pAg, pH values, etc, at suitable values during formation of the silver halide by precipitation.

The silver halide to be used in the invention may be advantageously subjected to chemical sensitization with noble metal (for example, gold) sensitizers, middle chalcogen (for example, sulfur) sensitizers, reduction sensitizers and others known in the art. Compounds and techniques useful for chemical sensitization of silver halide are known in the art and described in Research Disclosure I and the references cited therein.

The photographic elements of the present invention, as is typical, provide the silver halide in the form of an emulsion. Photographic emulsions generally include a vehicle for coating the emulsion as a layer of a photographic element. Useful vehicles include both naturally occurring substances such as proteins, protein derivatives, cellulose derivatives (e.g., cellulose esters), gelatin (e.g., alkali-treated gelatin such as cattle bone or hide gelatin, or acid treated gelatin such as pigskin gelatin), gelatin derivatives (e.g., acetylated gelatin, phthalated gelatin, and the like), and others as described in Research Disclosure I. Also useful as vehicles or vehicle extenders are hydrophilic water-permeable colloids. These include synthetic polymeric peptizers, carriers, and/or binders such as poly(vinyl alcohol), poly(vinyl lactams), acrylamide polymers, polyvinyl acetals, polymers of alkyl and sulfoalkyl acrylates and methacrylates, hydrolyzed polyvinyl acetates, polyamides, polyvinyl pyridine, methacrylamide copolymers, and the like, as described in Research Disclosure I. The vehicle can be present in the emulsion in any amount useful in photographic emulsions. The emulsion can also include any of the addenda known to be useful in photographic emulsions. These include chemical sensitizers, such as active gelatin, sulfur, selenium, tellurium, gold, platinum, palladium, iridium, osmium, rhenium, phosphorous, or combinations thereof. Chemical sensitization is generally carried out at pAg levels of from 5 to 10, pH levels of from 5 to 8, and temperatures of from 30° to 80° C., as illustrated in Research Disclosure, June 1975, item 13452 and U.S. Pat. No. 3,772,031.

The silver halide may be sensitized by sensitizing dyes by any method known in the art, such as described in Research Disclosure I. The dye may be added to an emulsion of the silver halide grains and a hydrophilic colloid at any time prior to (e.g., during or after chemical sensitization) or simultaneous with the coating of the emulsion on a photographic element. The dye/silver halide emulsion may be mixed with a dispersion of color image-forming coupler immediately before coating or in advance of coating (for example, 2 hours).

Photographic elements of the present invention are preferably imagewise exposed using any of the known techniques, including those described in Research Disclosure I, section XVIII. This typically involves exposure to light in the visible region of the spectrum.

Photographic elements comprising the composition of the invention can be processed in any of a number of well-known photographic processes utilizing any of a number of well-known processing compositions, described, for example, in Research Disclosure I, or in James, The Theory of the Photographic Process 4th, 1977. In the case of processing a reversal color element, the element is first treated with a black and white developer followed by treatment with a color developer. Preferred color developing agents are p-phenylenediamines. Especially preferred are:

4-amino N,N-diethylaniline hydrochloride, 4-amino-3-methyl-N,N-diethylaniline hydrochloride, 4-amino-3-methyl-N-ethyl-N-(β-(methanesulfonamido) ethylaniline sesquisulfate hydrate, 4-amino-3-methyl-N-ethyl-N-(β-hydroxyethyl)aniline sulfate, 4-amino-3-β-(methanesulfonamido)ethyl-N,N-diethylaniline hydrochloride and 4-amino-N-ethyl-N-(2-methoxyethyl)-m-toluidine di-p-toluene sulfonic acid.

Development is followed by bleach-fixing, to remove silver or silver halide, washing and drying.

The present invention will be further described in the following Examples.

EXAMPLE 1

Preparation of Dye 1

Ultraviolet absorber dyes as required by the present invention may be prepared by analogy to the method below for preparation of Dye 1.

In the following example, the piperidine moiety functions as a leaving group and other leaving groups such as morpholine, methylthio, etc., could also be used to effect this reaction.

N-Ethyl-2-(1-piperidinyl)benoxazolium hexafluorophosphate (7.52 grams, 0.020 mole) and 3-pentadecyl-1-phenyl-2-pyrazolin-5-one (7.41 grams, 0.020 mole) were stirred in dry acetonitrile (60 mL) at 55° C. After 5 minutes, 1,8-diazabicyclo[5.4.0]undec-7ene (3.1 grams, 0.020) mole as added dropwise over a period of 5 minutes. The reaction mixture was stirred and heated for 20 minutes and poured into 600 mL water. The precipitated material was stirred for 15 minutes and kept overnight at 5° C. The product was collected by suction filtration and recrystallized three times from methanol. Yield: 2.9 grams. M.P. 86°–88° C. The product was confirmed by a proton NMR spectrum and its purity by combustion analysis and HPLC.

EXAMPLE 2

Photostability tests in solution

The ultraviolet absorbing compound to be tested was dissolved in an appropriate HPLC grade solvent at a concentration such that the absorbance (Optical Density) of the solution was approximately 1 in a 1 cm cell at the absorbance maximum of the longest wavelength absorbance band, which is usually about 340 nm. The solution was placed in a 1 cm four-sided optical glass cell equipped with a stopcock to prevent evaporation or change of atmosphere. The solution was suspended in the center of a Rayonet Photochemical Reactor (manufactured by the Southern New England Ultraviolet Co., Branford, Conn.) equipped with 16 RPR 3500 angstrom Rayonet lamps and irradiated. The absorbance was measured before irradiation and at various times during irradiation. A similar four-sided cell containing the same solvent as the sample cell was used in the reference beam. The spectra were taken on either Perkin Elmer Lambda 5, Lambda 9 or Lambda 15 spectrophotometers. The degradation of the samples was generally linear, and the degradation is reported in Table 1 as the percentage loss of density after 100 hours of radiation.

Loss of Density=$\{D(0\ hr)-D(100\ hr)\}/D(0\ hr)$ wherein "D (0 hr)" and "D (100 hr)" are the density before irradiation and after irradiation, respectively.

TABLE 1

| Compound | | 100 Hour Percent Loss of Density in MeOH |
|---|---|---|
| C1 | comparison | 10 |
| Dye 1 | invention | 3 |
| Dye 2 | invention | 2 |
| Dye 3 | invention | 4 |
| Dye 4 | invention | 4 |

Comparison ultraviolet absorber compound C1, which is a known ultraviolet absorber compound for photographic elements, has the following structure:

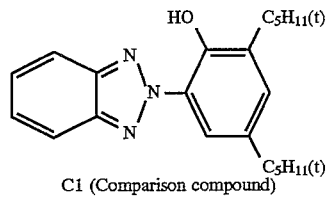

C1 (Comparison compound)

EXAMPLE 3

Molar Extinction Coefficients

The UV spectra of the compounds of the invention were compared with comparison ultraviolet absorber C1 and the results shown in Table 2 below. Note that each ultraviolet absorbing compound exhibited two absorbance peaks at less than 400 nm, and the extinction coefficient is given for both the shorter wavelength peak ("$\epsilon\lambda$(max hypso)") and the longer wavelength peak ("$\epsilon\lambda$(max batho)"). All spectra were obtained in methanol, using a Perkin Elmer Lambda 9 spectrophotometer. The molar extinction coefficient is a measure of the ability of a compound to absorb light. The compounds of the present invention have higher molar extinction coefficients than C1 and therefore less is required to achieve the same absorbance obtained with C1.

TABLE 2

| Compound | | $\epsilon\lambda$ (max hypso) | $\epsilon\lambda$ (max batho) |
|---|---|---|---|
| C1 | comparison | 15,700 (302 nm) | 15,200 (341 nm) |
| Dye 1 | invention | 18,600 (312 nm) | 24,200 (341 nm) |
| Dye 2 | invention | 31,400 (314 nm) | 26,700 (336 nm) |
| Dye 3 | invention | 40,100 (316 nm) | 31,900 (340 nm) |
| Dye 4 | invention | 19,000 (315 nm) | 26,300 (339 nm) |

The preceding examples are set forth to illustrate specific embodiments of this invention and are not intended to limit the scope of the compositions or materials of the invention. It will be understood that variations and modifications can be effected within the spirit and scope of the invention.

What is claimed is:

1. A photographic element comprising (a) at least one light-sensitive layer containing a light sensitive silver halide emulsion and (b) an ultraviolet absorbing compound with a peak absorption at less than 400 nm and being of formula (I):

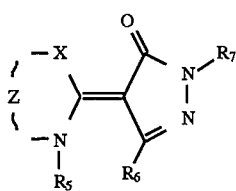

wherein:
X is O or $NR_8$, Z represents the atoms necessary to complete a 5-membered or 6-membered heterocyclic ring which includes X and N;

$R_5$ is alkyl or alkenyl any of which may be substituted or unsubstituted, or $R_5$ may form a ring with $R_6$;

$R_6$ is alkyl, alkenyl, aryl, heterocycle, alkoxycarbonyl, aryloxycarbonyl, alkoxy, aryloxy, sulfonamide, or imino, any of which may be substituted or unsubstituted, or hydrogen, hydroxy, cyano or halogen;

$R_7$ is alkyl, alkenyl, aryl, or heterocycle, any of which may be substituted or unsubstituted, or H; and $R_8$ is alkyl, or alkenyl any of which may be substituted or unsubstituted; or H; wherein the ultraviolet absorbing compound is substantially inert such that less than 50%, of the compound, by weight, is destroyed or otherwise removed on processing of the photographic element.

2. A photographic element comprising (a) at least one light-sensitive layer containing a light sensitive silver halide emulsion and (b) a substantially inert ultraviolet absorbing compound with a peak absorption at less than 400 nm and being of formula (Ia):

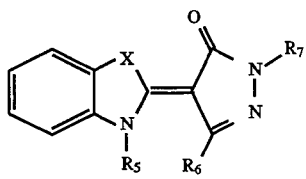

wherein:
X is O or $NR_8$, and the benzo ring may be substituted or unsubstituted;

$R_5$ and $R_8$ are, independently, alkyl or alkenyl any of which may be substituted or unsubstituted, or $R_5$ may form a ring with $R_6$ or a 4-position substituent on the benzo ring;

$R_6$ is alkyl, alkenyl, aryl, heterocycle, alkoxycarbonyl, aryloxycarbonyl, alkoxy, aryloxy, sulfonamide, or imino, any of which may be substituted or unsubstituted, or hydrogen, hydroxy, cyano or halogen;

$R_7$ is alkyl, alkenyl, aryl, or heterocycle, any of which may be substituted or unsubstituted, or H; and $R_8$ is alkyl, or alkenyl any of which may be substituted or unsubstituted, or H; wherein the ultraviolet absorbing compound is substantially inert such that less than 50%, of the compound, by weight, is destroyed or otherwise removed on processing of the photographic element.

3. A photographic element according to claim 1 additionally comprising a non-light sensitive layer not containing any light-sensitive silver halide emulsion, the ultraviolet absorber of formula (I) being located in the non-light sensitive layer.

4. A photographic element according to claim 1 wherein the amount of the ultraviolet compound of formula (I) is between 0.10 g/m² to 2.0 g/m².

5. A photographic element according to claim 1 wherein the amount of ultraviolet absorber of formula (I) in any layer containing light sensitive silver halide is less than $10^{-8}$ moles per mole of silver halide.

6. A photographic element according to claim 3 additionally comprising a support, wherein the non-light sensitive layer in which the ultraviolet absorber of formula (I) is located, is above all light-sensitive layers of the element.

7. A photographic element comprising (a) at least one light-sensitive layer containing a light sensitive silver halide emulsion and (b) an inert ultraviolet absorbing compound with a peak absorption at less than 400 nm and being of formula (Ib):

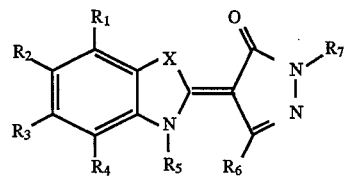

wherein:
X is O or $NR_8$;

$R_1$, $R_2$, $R_3$, and $R_4$ may be the same or different and any of them may be alkyl, alkenyl, aryl, heterocycle, alkoxycarbonyl, aryloxycarbonyl, alkoxy, aryloxy, sulfonamide, amino, imino, or amido, any of which may be substituted or unsubstituted, or hydrogen, hydroxy, cyano, or halogen, or combinations of $R_1$ to $R_4$ can be taken to form an alicyclic, carbocyclic or heterocyclic ring;

$R_6$ is alkyl, alkenyl, aryl, heterocycle, alkoxycarbonyl, aryloxycarbonyl, alkoxy, aryloxy, sulfonamide, or imino, any of which may be substituted or unsubstituted, or hydrogen, hydroxy, cyano or halogen;

$R_5$ is alkyl or alkenyl any of which may be substituted or unsubstituted, or $R_5$ may form a ring with $R_4$ or $R_6$;

$R_7$ is alkyl, alkenyl, aryl, or heterocycle, any of which may be substituted or unsubstituted, or H; and $R_8$ is alkyl or alkenyl any of which may be substituted or unsubstituted, or H.

8. A photographic element according to claim 7 additionally comprising a support, and a non-light sensitive layer positioned above all light sensitive layers and which does not contain any light-sensitive silver halide emulsion, and wherein the ultraviolet absorber of formula (I) is located in the non-light sensitive layer.

9. A photographic element according to claim 8 wherein the amount of the ultraviolet compound of formula (I) is between 0.1 g/m² to 2.0 g/m².

10. A photographic element according to claim 8 wherein the amount of the ultraviolet compound of formula (I) is between 0.5 g/m² to 1 g/m².

11. A photographic element according to claim 7 wherein the ultraviolet absorber is of formula (Ic):

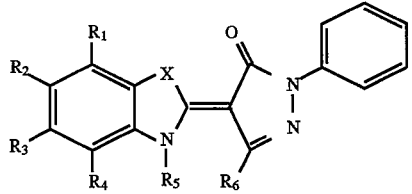

wherein and each of X and $R_1$ to $R_6$ has the same meaning as in formula (Ib) and the N-phenyl ring shown may be substituted or unsubstituted.

12. A photographic element according to claim 1 wherein all of the light sensitive layers of the element do not contain any surface fogged silver halide emulsion.

13. A photographic element according to claim 1 wherein the element has been exposed to light and processed with at least a silver halide developer and fixer to obtain a silver image or a dye image.

14. A photographic element according to claim 7 wherein the element has been exposed to light and processed with at least a silver halide developer and fixer to obtain a silver image or a dye image.

15. A photographic element according to claim 10 wherein the element has been exposed to light and processed with at least a silver halide developer and fixer to obtain a silver image or a dye image.

16. A method of developing the photographic element of claim 1, which element has been exposed to light, comprising processing the element to obtain a final negative image.

17. A method of forming a photographic element according to claim 3 comprising coating the light-sensitive layer on an element portion comprising at least a base, and also coating the non-light sensitive layer containing the ultraviolet absorber.

18. A method according to claim 17 wherein the non-light sensitive layer containing the ultraviolet absorber is coated above all light sensitive layers.

\* \* \* \* \*